United States Patent
Mehl, Sr.

[11] Patent Number: 5,846,252
[45] Date of Patent: *Dec. 8, 1998

[54] METHOD OF REMOVING HAIR FROM THE BODY AND INHIBITING FUTURE GROWTH

[76] Inventor: Thomas L. Mehl, Sr., 4020 Newberry Rd. Suite 400, Gainesville, Fla. 32607

[ * ] Notice: The term of this patent shall not extend beyond the expiration date of Pat. No. 5,364,394.

[21] Appl. No.: 555,996

[22] Filed: Nov. 15, 1995 Related U.S. Application Data60

[22] Filed: Provisional application No. 60/013,374 Mar. 15, 1996.

Related U.S. Application Data

[63] Continuation-in-part of PCT/US94/14557 Dec. 30, 1994 published as WO95/19856 Jul. 6, 1995, continuation of Ser. No. 917,662, Jul. 20, 1992, abandoned, which is a continuation of Ser. No. 794,364, Nov. 13, 1991, abandoned, which is a continuation of Ser. No. 454,622, Dec. 21, 1989, abandoned, and Ser. No. 176,561, Dec. 30, 1993, Pat. No. 5,470,332, which is a continuation of Ser. No. 066,261, May 25, 1993, abandoned, which is a continuation of Ser. No. 929,750, Aug. 17, 1992, abandoned, which is a continuation of Ser. No. 707,828, May 30, 1991, abandoned.

[51] Int. Cl.[6] ................................................. A61B 17/50
[52] U.S. Cl. .......................... 606/133; 606/131; 606/36
[58] Field of Search .............................. 606/133, 1, 36, 606/40, 131, 43

[56] References Cited

U.S. PATENT DOCUMENTS

| | | |
|---|---|---|
| 2,888,927 | 6/1959 | Fozard . |
| 3,054,405 | 9/1962 | Tapper . |
| 3,999,552 | 12/1976 | Huggins . |
| 4,033,350 | 7/1977 | Hoshi . |
| 4,174,714 | 11/1979 | Mehl . |
| 4,274,413 | 6/1981 | Hahn et al. . |
| 4,311,145 | 1/1982 | Esty et al. . |
| 4,317,450 | 3/1982 | Chalmers et al. ........................ 606/36 |
| 4,498,474 | 2/1985 | Chalmers et al. . |
| 4,566,454 | 1/1986 | Mehl et al. . |
| 4,617,926 | 10/1986 | Sutton .................................... 606/133 |
| 5,026,369 | 6/1991 | Cole ......................................... 606/36 |
| 5,049,148 | 9/1991 | Mehl . |
| 5,059,192 | 10/1991 | Zaias . |
| 5,133,712 | 7/1992 | McPherson . |
| 5,169,398 | 12/1992 | Glaros . |
| 5,211,941 | 5/1993 | Komori et al. ........................... 424/70 |
| 5,226,907 | 7/1993 | Tankovich . |
| 5,364,394 | 11/1994 | Mehl et al. .............................. 606/36 |
| 5,425,728 | 6/1995 | Tankovich ................................. 606/9 |

FOREIGN PATENT DOCUMENTS

| | | |
|---|---|---|
| 0484463 | 6/1990 | European Pat. Off. . |
| 2383675 | 11/1978 | France . |
| 2590791-A | 6/1987 | France . |
| 3202962-A | 12/1983 | Germany . |

*Primary Examiner*—Robert A. Hafer
*Assistant Examiner*—Justine R. Yu
*Attorney, Agent, or Firm*—Shlesinger, Arkwright & Garvey LLP

[57] ABSTRACT

Method for the very rapid removal of hair through the use of electromagnetic (e.g., AC, DC, blend, and laser) energy by treatment of the hair prior to the application of such electromagnetic energy to reduce the electromagnetic energy resistance of the hair. Such hair treatment may include applying conductive solutions, pre-treating the hair to yield an alkaline environment (i.e., hair is made more alkaline), and adding graphite, metal, conductive non-metal solids, viscous materials, and liquids, for example.

22 Claims, 4 Drawing Sheets

5,846,252

METHOD OF REMOVING HAIR FROM THE BODY AND INHIBITING FUTURE GROWTH

CROSS REFERENCE TO RELATED APPLICATIONS

This application is a continuation in part of application Ser. No. PCT/US94/14557, filed Dec. 30, 1994, now published international application no. WO 95/17856, published Jul. 6, 1995, and which claims the priority of application Ser. No. 08/176,561, filed Dec. 30, 1993, now U.S. Pat. No. 5,470,332, issued Nov. 28, 1995, which is a continuation of application Ser. No. 07/917,662, filed Jul. 20, 1992, now abandoned, which is a continuation of application Ser. No. 07/794,364, filed Nov. 13, 1991, now abandoned, which is a continuation of application Ser. No. 07/454,622, filed Dec. 21, 1989, now abandoned, and application Ser. No. 08/176, 561, filed on Dec. 30, 1993, now U.S. Pat. No. 5,470,332, issued Nov. 28, 1995, likewise is a continuation of application Ser. No. 08/066,261, filed May 25, 1993, now abandoned, which is a continuation of application Ser. No. 07/929,750, filed Aug. 17, 1992, now abandoned, which is a continuation of application Ser. No. 07/707,828, filed May 30, 1991, now abandoned, and each of which is incorporated herein by reference.

FIELD OF THE INVENTION

This invention relates to an electromagnetic energy hair removal method and device which more effectively and permanently impairs future hair regrowth.

BACKGROUND OF THE INVENTION

Recent hair removal or epilator devices currently in use are tweezers type units through which radio frequency (RF) energy is applied to the hair shaft.

Typical of such devices and methods for removal of hair are described in Mehl U.S. Pat. Nos. 4,174,713; 4,566,454; and Mehl Pending applications Ser. No.372,852, filed Jun. 29, 1989, each of which is incorporated herein by reference. The methods taught in the above-mentioned patents and applications require in many instances thirty seconds treatment of each hair to be removed. Sufficient time was required in order to effectively damage the root system of the hair so that the hair may be removed by a very gentle upward lift rather than by the sharp tug which would be normally applied for the removal of a single hair by a tweezers without any treatment of the hair.

U.S. Pat. No. 4,566,454, to Mehl et al., discloses utilizing the resonant frequency of hair in conjunction with RF, and is incorporated herein by reference.

More recently, an even faster hair removal system which, by use of RF energy, yielded damage to the root in less than half the time required by earlier methods is disclosed in U.S. Pat. No. 5,364,394, Mehl, which is incorporated herein by reference.

There are likewise known U.S. Pat. Nos 5,425,728 and 5,226,907 to Tankovich, which disclose using the wave energy of a laser in conjunction with hair removal by the application of a contaminant oil on the skin.

OBJECTS AND SUMMARY OF INVENTION

It is an object of this invention to provide a method for removing hair more effectively using electromagnetic energy, such as alternating current (AC), direct current (DC), DC-biased RF (so-called "blend") and laser energy by treating the hair to make the hair more conductive to electromagnetic energy and/or tuning the resonant frequency of the hair to the wavelength of the electromagnetic wave energy and thereby reduce the time necessary to sufficiently damage the root of the hair to cause it to release the hair from the body so that it may be removed.

Another object of this invention is to achieve the present treatment time for removal of each hair when using AC, DC, blend, and laser energy as has been realized with RF energy, and to even reduce the time as much as one-half to one-quarter or even less of the amount of time presently needed to effectively remove the hair.

Yet another object of this invention is to provide a method for removing the hair in and which application Ser. No. 08/176,561 the hair is pretreated prior to the application of electromagnetic energy (e.g. AC, DC, blend, and laser), to make it more receptive to the electromagnetic energy and to make it reduce dissipation of the electromagnetic energy prior to its reaching the root of the hair.

A further object of this invention is provide a method of pretreating the hair prior to the application of electromagnetic (e.g., AC, DC, blend, laser) energy which is inexpensive and does not require specialized training for the individual utilizing the method.

Still a further object of this invention is to provide a method for removing hair which can be applied to all of the hair to be removed at one time prior to the application of wave energy.

Another object of this invention is to provide a method for treating the hair which will permit the use of existing electromagnetic wave energy hair removal devices (including RF devices) such as disclosed in U.S. Pat. No. 5,364,394 to Mehl, and U.S. Pat. No. 5,059,192 to Zaias, both incorporated herein by reference, without requiring modification of the same.

Still a further object of this invention is to provide a method of removing hair which does not require the hair to be trimmed prior to the application of electromagnetic (e.g., AC, DC, blend, laser) energy as was required in the past.

A further object of this invention is to provide a method for removing hair which will not cause discomfort to the individual and will not burn the outer tissues of the skin and cause discomfort to the person whose hair is being removed.

Another object of this invention is to provide a shorter path for the electromagnetic (e.g., AC, DC, blend, laser) energy through the hair from the external surface by enlarging the thickness of the cuticle of the hair by the treatment of the hair cuticle prior to application of the electromagnetic energy.

In summary, this invention provides a new method for the very rapid removal of hair through the use of electromagnetic (e.g., AC, DC, blend, laser) energy by treatment of the hair prior to the application of electromagnetic energy.

These and other objects and features of this invention will be apparent from the following description and claims.

DESCRIPTION OF THE INVENTION

Figure 1:
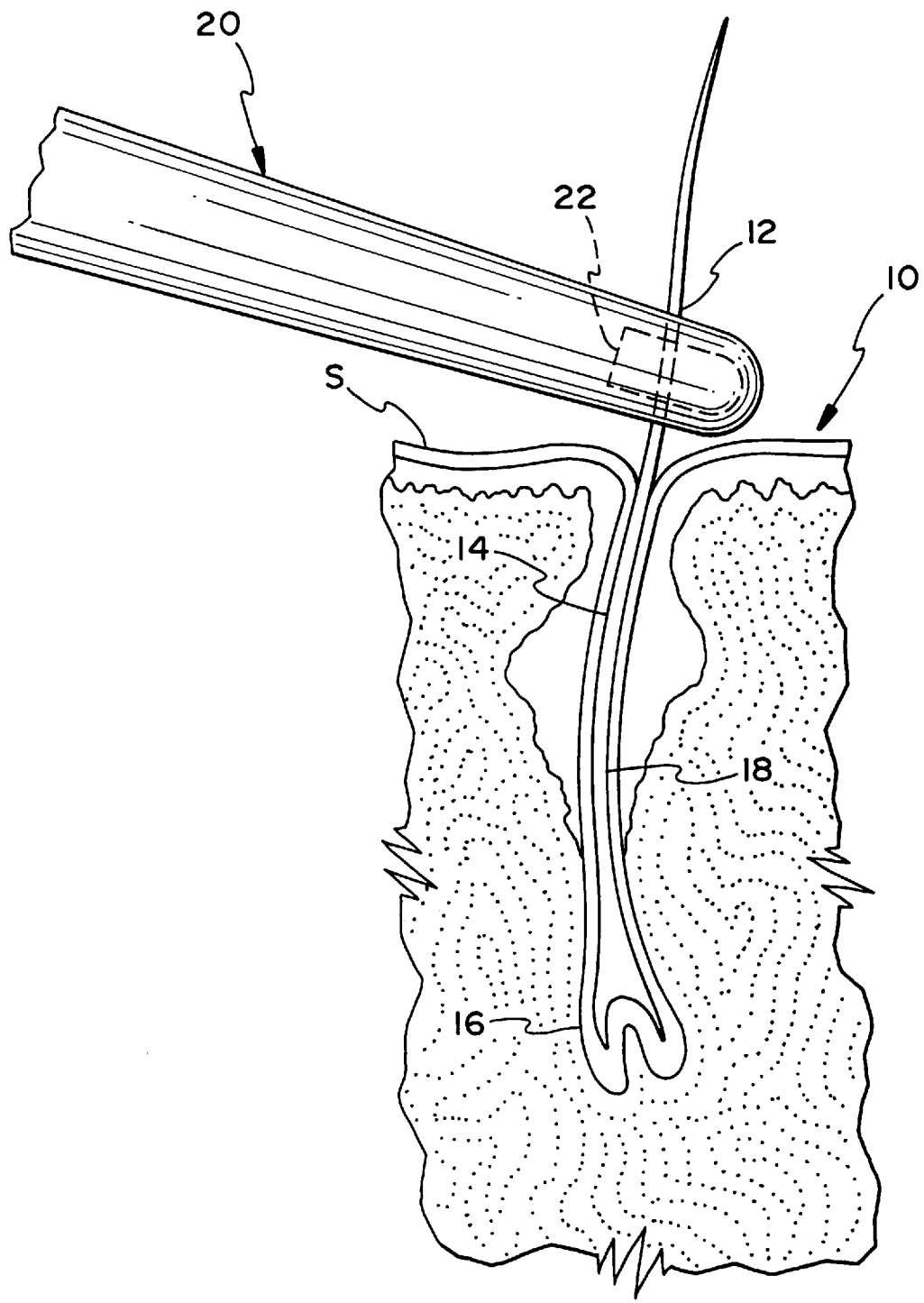
FIG. 1 is a fragmentary cross-sectional view of a hair in position within a tissue and showing it held between engaging ends of an electromagnetic wave energy power transmission tweezers.
Figure 2:
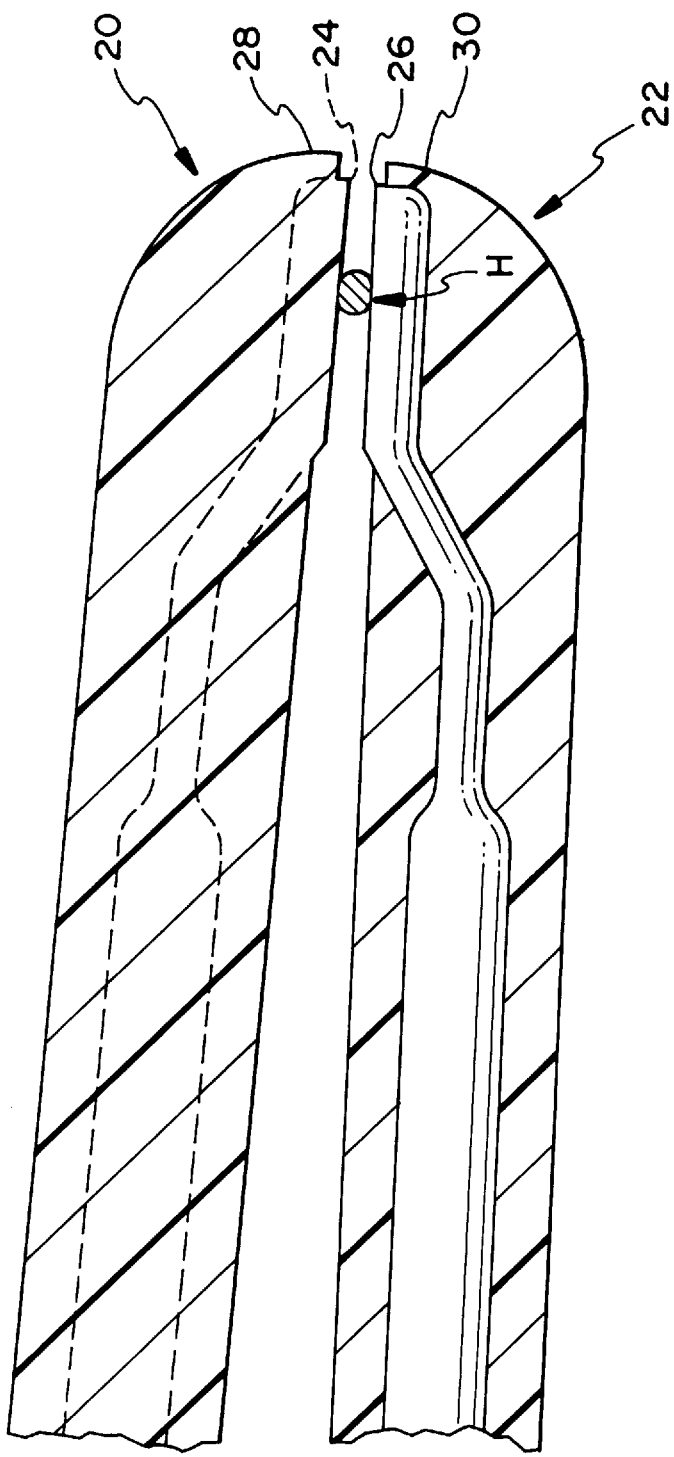
FIG. 2 is a fragmentary cross-sectional view of the tweezers shown in FIG. 1, in use, with the tips engaging a hair shaft.

Referring particularly to both FIGS. 1 and 2, a section of the tissue containing a hair is generally indicated at 10 with the external portion of the hair 12 extending upwardly from the skin surface S, while the internal portion of the hair shaft 14 extends downwardly to the hair follicle 16. The hair has a central core section 18 which conducts electromagnetic wave energy along the length of the hair shaft portion 12 and 14 to the follicle 16 by way of the central core section 18.

Electromagnetic energy is also conducted along the outer surface of hair 12, as well as inner portions thereof, dependent on the wavelength and/or resonant frequency thereof, and the type of pretreatment of the hair, for example, as will be readily appreciated.

The external section of the hair shaft 12 is shown grasped between two opposed tweezers arm ends 20 and 22. The two opposed tweezers arm ends 20 and 22 are similar in construction and may carry opposed metal electromagnetic energy conduction tweezers pads 24 and 26 which act as hair engaging surfaces.

As illustrated in FIG. 2, pad 24 is shown in phantom lines to indicate that pad 24 may be deleted as only one wave energy pad, such as 26 may be required, such as when using DC-biased RF, the so-called blend, and various wavelengths and power levels of AC, DC, and laser (i.e., electromagnetic energy outside the RF spectrum), as well as RF described in U.S. Pat. No. 5,364,394 to Mehl. Thus, the tweezer arm 22 would have a plastic extending area to fill the void of the unnecessary pad 24. The hair shaft H is shown in FIG. 2 grasped between the pads 24 and 26. Dielectric insulation 28 and 30 surrounds the hair engaging surfaces of the pads 24 and 26 to provide electromagnetic wave energy insulation and focussing, and also to prevent burning the skin when applying such wave energy. Further details of the tweezers are shown in the Mehl patents and applications referred to above.

Figure 3:
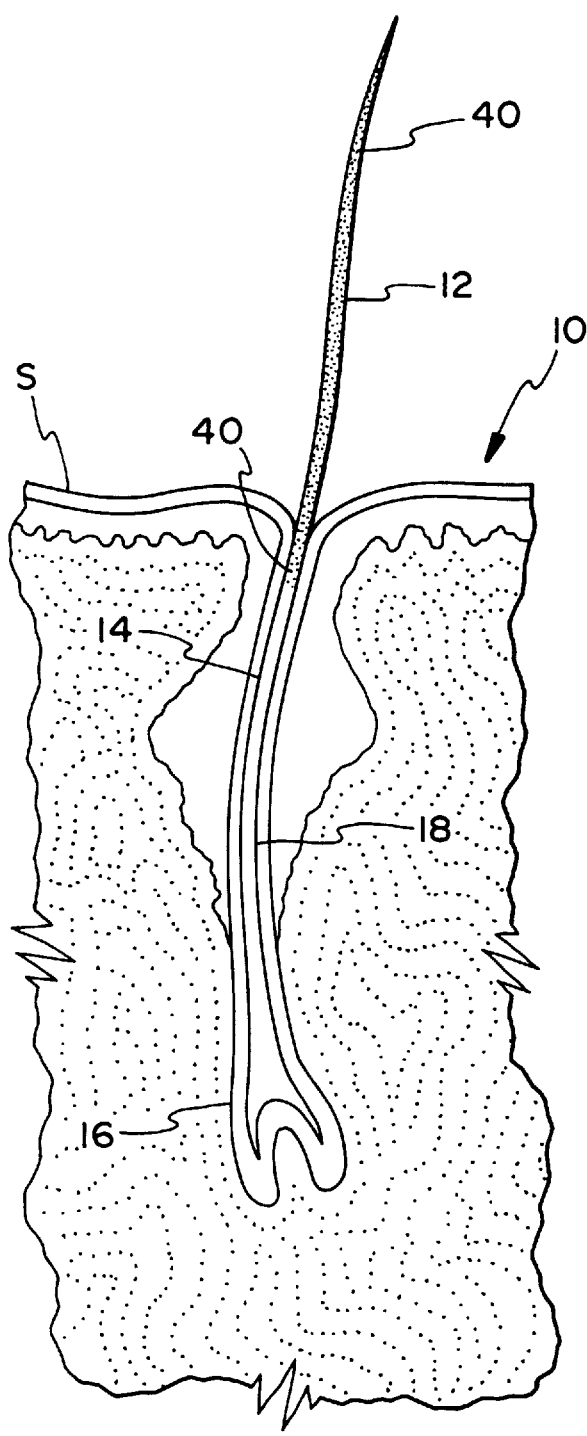
FIG. 3 is a fragmentary cross-sectional view of a hair within a tissue, and showing it with absorbed material.

FIG. 3 illustrates a typical hair which has been pretreated prior to treatment with electromagnetic energy and subsequent removal of the thus damaged/killed hair.

Material 40 has been added to the hair for absorption thereby. Such material 40 is conductive material from a conductive solution, or a liquid crystal for fine-tuning the resonant frequency of the hair, or both. As will be readily appreciated, some of material 40 may be absorbed by the hair for a distance below the surface of the skin. No pair of tweezers 20 is required when the electromagnetic energy is applied in the form of wave energy from a laser beam for example. In that case, the characteristics of the liquid crystal are selected so as to compliment the wavelength of the laser beam which will be used to heat up the hair for damage/destruction thereof. When blend is used, both electrically conductive solution/material and liquid crystal are used to enhance the effectiveness of the electromagnetic wave energy component of blend (i,e, the RF component of the DC-biased RF)

It is to be noted in FIG. 1 that the hair shaft extends beyond the tweezers normally and with the method of this invention need not be cut down as previously noted in the attached aforementioned patents and applications.

Figure 4:
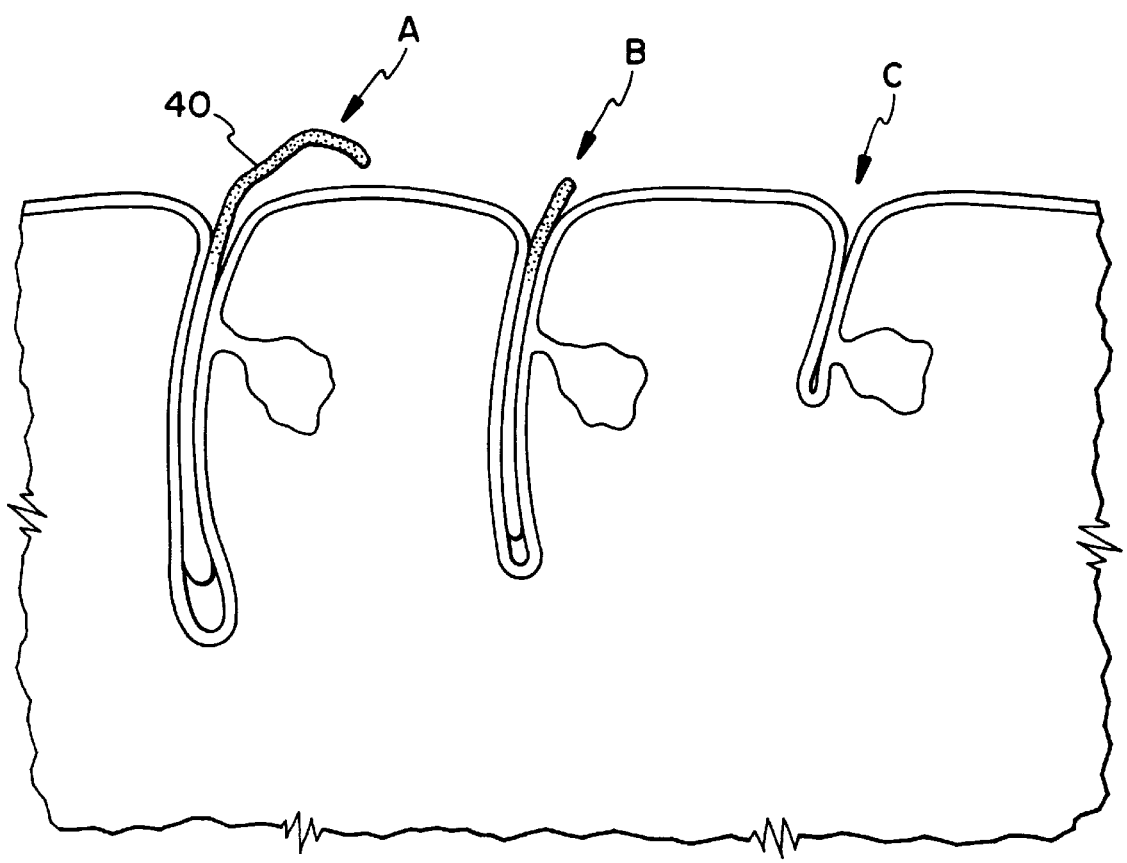
FIG. 4 is similar to FIG. 3, showing the destruction of a treated hair.

FIG. 4 shows the hair immediately after treatment with initial shrinkage of the hair components (at arrow A), the further shrinkage and destruction of the hair (at arrow B), and the final state (at arrow C), when the hair is completely removed (as by washing away or removed by traditional pulling thereof).

Additional tweezers and power sources suited for the transmission of AC, DC, RF, and blend into clamped hairs are shown and described in FIGS. 13–17 and the related text, for example, of related Mehl application PCT/US94/14557, filed 30 Dec., 1994, and which is incorporated herein by reference.

Experimental results have shown that AC, DC, blend, and laser energy (at far lower levels than previously thought possible) successfully allowed hair to be removed faster.

As has been noted above, the method of removing the hair from the body described in this invention often requires a pretreatment of the hair prior to the application of the electromagnetic energy.

It has been found that treating the hair with an appropriate electromagnetic wave energy conductive material produces substantially improved results in both time required to gently remove the hair as well as more effective destruction of hair root.

It has been found that pretreatment of the hair to yield an alkaline environment (i.e., the hair to be removed has been rendered somewhat alkaline) provides improved results.

It has been found that treatment of the hair with an electrically conductive material yields manifold increases in the effects of the electromagnetic wave energy applied to the hair and hastens the destruction of the hair root and the ease of release of the hair. Thus, such treated hairs can be gently removed without tugging as in the case of normal plucking of a hair from the body without the benefit of pretreatment with such wave energy.

The treatment often requires the application of an electromagnetic energy conductive material such as graphite, metal or a conductive non-metal including solids, viscous materials, liquids and the like. Water soluble inorganic and organic salts, acids, and the bases may be used so long as they are weak and will not damage the skin tissue. A 0.5% to 1.5% water solution of a soluble salt acid or base has been found effective with conductive acids salts and bases. Standard chemistry books will indicate the conductivity of various acids, bases and salts such as gold chloride, silver chloride, copper chloride, and the like as well as 1% solutions of acids, such as acidic, citric, oxalic, and lactic are also effective. 1% solutions of ammonium hydroxide, and other conductive bases may be used.

Pretreatment to yield an alkaline environment/hair has been successfully used, as described above.

Conductive ointments or salves such as used by physicians in cardiology in EKG (i.e., electrocardiogram) equipment and the like which are conductive and available on the market may also be used. The application of conductive mineral powders may also be used to treat the hair although such mineral powders are more difficult to use than solutions such as described above.

Graphite is an example of mineral powder that can be impregnated into and on the hair cuticle to enhance the conductivity of the electromagnetic wave energy. Another compound that works is silver nitrate.

Preliminary cleaning and pretreatment of the hair to be removed is discussed at length in columns 3–4 of U.S. Pat. No. 5,364,394 to Mehl, for example.

Upon the application of the conductive material to the hair, the cuticle or outer hard portion of the hair which is somewhat porous picks up the material and provides for more rapid conduction of the electromagnetic energy directly to the core and thence to the hair root for destruction and damage to the same.

A liquid crystal may also be used to enhance the treatment of the hair. Upon the application of the liquid crystal to the hair, combined with other electrically conductive materials and the application of a laser beam to the hair, electromagnetic energy is delivered to the hair root to hasten destruction of the growth area and ease the release of the hair.

Once the hair has been treated with the electromagnetic wave energy conductive material, the electromagnetic wave energy is applied by means of a laser source, or the like, to the hair. A gentle lifting upward of the hairs instantly after treatment yields effective removal of the hair. Or the treated hair can be washed or wiped away, for example.

The average time for treatment is comparable to the treatment time for RF treated hair or less.

U.S. Pat. No. 4,566,454 talks about utilizing resonant frequency using RF energy and U.S. Pat. No. 5,364,394 describes impregnating the hair with a conductive material such as conductive metal, conductive solution such as metal salt and acid or a base.

In the present inventions, by combining the resonant frequency of hair to laser hair removal, and impregnating the hair with a conductive solution and a liquid crystal pre-tuned to the frequency of any laser, we can instantly transfer the laser energy to the hair by resonating the exact frequency used by that laser already pretuned to the liquid crystal impregnated into the hair, thereby to generate heat in the hair in sufficient amount to damage/kill the papilla hair root and the surrounding/associated cells to cause hair damage/death, but without causing any damage to the surrounding cells.

It has been known that different types of hair and hair colors have required more or less electromagnetic wave energy to permit removal of the hair and to inhibit future growth. Treatment of the hair with a conductive material has shown to be substantially equally effective on all types of hair as to the time required for removal thereof.

While this invention has been described as having a preferred design, it is understood that it is capable of further modifications, and uses and/or adaptations of the invention and following in general the principles of the invention and including such departures from the present disclosure as come within the known or customary practice in the art to which the invention pertains, and as may be applied to essential features hereinbefore set forth, and fall within the scope of the invention or limits of the claims appended hereto.

What is claimed is:

1. The method of removing a hair from a skin surface of an individual and inhibiting future growth by causing the hair to be sufficiently damaged at its root so as to be more readily releasable at its roots and removable by a very gentle force rather than by the normal force required to pluck a non-treated hair from the skin surface, comprising steps of:
    a) treating the hair to reduce electromagnetic energy resistance of the hair to permit more electromagnetic energy outside the RF spectrum during an entire treatment time to travel along the hair to reach the hair root;
    b) firmly grasping the hair between a pair of opposed electromagnetic energy conducting hair engaging surfaces carried by a pair of electromagnetic energy insulated members at a point relatively close to but clear of and above the skin surface of the grasped hair;
    c) applying electromagnetic outside the RF spectrum energy to at least said one of said hair engaging surfaces;
    d) holding said hair engaging surfaces in firm engagement with said hair while applying focussed electromagnetic energy outside the RF spectrum to travel along the hair and to damage the hair root sufficiently to permit the hair to be removed by a very gentle upward lift; and,
    e) applying an upward lifting force to the hair by the hair engaging surfaces during application of said electromagnetic energy outside the RF spectrum, said upward lifting force being less than the force of a tug ordinarily required for removal of non-treated hair.

2. The method of claim 1 and wherein:
    the step of treating the hair includes impregnating the outer surface of the hair with an electromagnetic energy conductive material.

3. The method of claim 1 and including the step of:
    using electromagnetic energy conductive material in the form of a liquid.

4. The method of claim 1, wherein:
    in said step of applying electromagnetic energy outside the RF spectrum, said energy is in the form of laser energy.

5. The method of claim 1, wherein:
    in said step of applying electromagnetic energy outside the RF spectrum, said energy is in the form of DC energy.

6. The method of claim 1, wherein:
    in said step of applying electromagnetic energy outside the RF spectrum, said energy is in the form of AC energy.

7. The method of claim 1, wherein:
    in said step of firmly grasping the hair, said pair of electromagnetically insulated members includes a pair of tweezers.

8. The method of claim 1, wherein:
    said at least one electromagnetic energy conducting surface includes a pad; and
    said pair of energy insulated members includes a pair of tweezers.

9. The method of removing a hair from a skin surface of an individual and inhibiting future growth by causing the hair to be sufficiently damaged at its root so to be more readily releasable at its roots and removable by a very gentle force rather than by the normal force required to pluck a non-treated hair from the skin surface, comprising the steps of:
    a) treating the hair with a liquid crystal to reduce eletromagnetic wave energy resistance of the hair to permit more eletromagnetic wave energy outside the RF spectrum during an entire treatment time to be absorbed by the hair, and to be converted to heat energy which travels along the hair to reach the hair root;
    b) applying focussed electromagnetic wave energy outside the RF spectrum to strike the hair and to generate heat energy to damage the hair root sufficiently to permit the hair to be removed; and,
    c) applying an upward lifting force to the hair for removal thereof, said upward lifting force being less than the force of the tug ordinarily required for removal of non-treated hair.

10. The method of claim 9, wherein:
    in said step of applying electromagnetic wave energy outside the RF spectrum, said wave energy is in the form of laser energy.

11. The method of claim 9, wherein:
    the step of treating the hair includes impregnating the outer surface of the hair with an electromagnetic energy conductive material.

12. The method of claim 9, and including the step of:

using electromagnetic energy conductive material in the form of a liquid.

13. The method of claim 8, wherein:

in said step of applying electromagnetic energy outside the RF spectrum, said energy is in the form of laser energy.

14. The method of claim 9, wherein:

in said step of applying electromagnetic energy outside the RF spectrum, said energy is in the form of AC energy.

15. The method of removing a hair from a skin surface of an individual and inhibiting future growth by causing the hair to be sufficiently damaged at its root so to be more readily releasable at its roots and removable by a force less than the force required to pluck a non-treated hair from the skin surface, comprising the steps of:

a) treating the hair with a liquid crystal to reduce electromagnetic wave energy resistance of the hair to permit more electromagnetic wave energy outside the RF spectrum during an entire treatment time to be absorbed by the hair, and to be converted to heat energy which travels along the hair to reach the hair root;

b) applying focussed electromagnetic wave energy outside the RF spectrum to strike the hair and to generate heat energy to damage the hair root sufficiently to permit the hair to be removed; and c) applying an upward lifting force to the hair for removal hereof, said upward lifting force being less than the force of the tug ordinarily required for removal of non-treated hair.

16. The method of claim 15, wherein:

the step of treating the hair includes impregnating the outer surface of the hair with an electromagnetic energy conductive material.

17. The method of claim 15, including the step of:

using electromagnetic energy conductive material in the form of a liquid.

18. The method of claim 15, wherein:

in said step of applying electromagnetic energy outside the RF spectrum, said energy is in the form of laser energy.

19. The method of claim 15, wherein:

in said step of applying electromagnetic energy outside the RF spectrum, said energy is in the form of AC energy.

20. The method of removing a hair from a skin surface of an individual and inhibiting future growth by causing the hair to be sufficiently damaged at its root so as to be more readily releasable at its roots and removable by a force less than the normal force required to pluck a non-treated hair from the skin surface, comprising steps of:

a) treating the hair to reduce electromagnetic energy resistance of the hair to permit more electromagnetic energy outside the RF spectrum during an entire treatment time to travel along the hair to reach the hair root;

b) applying focussed electromagnetic energy outside the RF spectrum to travel along the hair and to damage the hair root sufficiently to permit the hair to be removed by a force less than the normal force required to remove non-treated hair; and, c) removing the hair by applying force to the hair less than the force required for removal of non-treated hair.

21. The method of claim 20, wherein:

a) the step of treating the hair includes impregnating the outer surface of the hair with an electromagnetic energy conductive material.

22. The method of claim 20, wherein:

the step of removing the hair is performed substantially at the same time as the step of applying focussed electromagnetic energy outside the RF spectrum.

\* \* \* \* \*